(12) United States Patent
Hegazi et al.

(10) Patent No.: US 8,742,340 B2
(45) Date of Patent: Jun. 3, 2014

(54) METHODS OF PREPARING LIQUID BLENDS FOR BUILDING CALIBRATION CURVES FOR THE EFFECT OF CONCENTRATION ON LASER-INDUCED FLUORESCENCE INTENSITY

(71) Applicant: Saudi Arabian Oil Company, Dhahran (SA)

(72) Inventors: Ezzat Mahmoud Hegazi, Dhahran (SA); Abdullah H. Al-Grainees, Dammam (SA)

(73) Assignee: Saudi Arabian Oil Company (SA)

( * ) Notice: Subject to any disclaimer, the term of this patent is extended or adjusted under 35 U.S.C. 154(b) by 0 days.

(21) Appl. No.: 13/914,110

(22) Filed: Jun. 10, 2013

(65) Prior Publication Data
US 2013/0270455 A1 Oct. 17, 2013

Related U.S. Application Data

(62) Division of application No. 12/815,465, filed on Jun. 15, 2010, now Pat. No. 8,481,930.

(51) Int. Cl.
| | | |
|---|---|---|
| *G01T 1/167* | (2006.01) | |
| *G01T 1/169* | (2006.01) | |
| *G01N 31/00* | (2006.01) | |
| *G01N 33/03* | (2006.01) | |
| *G01N 33/26* | (2006.01) | |

(52) U.S. Cl.
USPC ............ 250/301; 250/252.1; 250/461.1; 250/339.09; 250/339.12; 422/82.08; 436/60; 436/172; 356/318

(58) Field of Classification Search
CPC ............ G01N 33/2829; G01N 33/28; G01N 33/2835; G01N 21/3103; G01N 21/314; G01N 21/35; G01N 21/3577; G01N 21/05; G01N 21/274; G01N 21/64; G01N 21/6402; G01N 21/6408; G01N 21/6428; G01N 21/643; G01N 21/645; G01N 2021/6421; G01N 2021/6491; G01N 2021/6482; G01J 1/58; G01J 3/30; G01J 3/42; G01J 3/44; G01J 3/4406; G01J 1/429
USPC ............ 250/458.1, 459.1, 372, 373, 461.1, 250/252.1, 301, 339.09, 339.12; 356/317, 356/318, 417; 422/82.07, 82.08; 436/171, 436/172, 60

See application file for complete search history.

(56) References Cited

U.S. PATENT DOCUMENTS

| | | | | |
|---|---|---|---|---|
| 4,278,444 A | * | 7/1981 | Beyer et al. | ............ 44/437 |
| 5,192,984 A | * | 3/1993 | Beecher et al. | ............ 356/433 |

(Continued)

OTHER PUBLICATIONS

Digambara et al. "Effect of sample geometry on synchronous fluorimetric analysis of petrol, diesel, kerosene, and their mixtures at higher concentration". The Analyst, 125 (2000): 1383-1386.*

(Continued)

*Primary Examiner* — Michael G Lee
*Assistant Examiner* — Suezu Ellis
(74) *Attorney, Agent, or Firm* — Bracewell & Giuliani LLP; Constance Gail Rhebergen; Brad Y. Chin (57) ABSTRACT

Disclosed herein are methods for determining and replicate unknown ratios of original target liquid blends, such as hydrocarbon fuel blends or contaminants, by using an in-process fluorescence-monitored procedure. The methods rely on trial-and-error mixing of the fuel ingredients into a single container. At the end of the trial-and-error procedure, the formed blend becomes an exact replica of the target fuel blend. The methods can also be used to build calibration curves without employing sets of previously prepared standard solutions.

8 Claims, 3 Drawing Sheets

(56) References Cited

U.S. PATENT DOCUMENTS

| | | | |
|---|---|---|---|
| 5,381,002 A * | 1/1995 | Morrow et al. | 250/301 |
| 5,424,959 A * | 6/1995 | Reyes et al. | 702/28 |
| 5,656,810 A * | 8/1997 | Alfano et al. | 250/301 |
| 6,633,043 B2 * | 10/2003 | Hegazi et al. | 250/461.1 |
| 6,881,381 B1 * | 4/2005 | Asher et al. | 422/68.1 |
| 6,952,259 B2 * | 10/2005 | Pible et al. | 356/318 |
| 7,501,285 B1 * | 3/2009 | Triche et al. | 436/139 |
| 7,659,512 B2 * | 2/2010 | Arakawa | 250/339.12 |
| 7,846,390 B2 * | 12/2010 | Hegazi | 422/82.05 |
| 8,045,154 B2 * | 10/2011 | Hegazi | 356/318 |
| 8,269,961 B2 * | 9/2012 | Mostowfi et al. | 356/246 |
| 8,557,589 B2 * | 10/2013 | Eccleston et al. | 436/60 |
| 2003/0141459 A1 | 7/2003 | Hegazi et al. | |
| 2007/0237679 A1 | 10/2007 | Hegazi | |
| 2008/0035858 A1 | 2/2008 | Hegazi | |

OTHER PUBLICATIONS

European Search Report dated Aug. 20, 2013; EP Application No. 13 17 6557.0-1554; Reference PM334343EPA.

Li, J., et al., Matching Fluorescence Spectra of Oil Spills with Spectra from Suspect Sources, XP-002662373, Analytica Chimic Acta, Jun. 30, 2004, pp. 51-56, vol. 514, www.elsevier.com/locate/aca, Elsevier B.V.

Christensen, J. H., et al., Characterization and Matching of Oil Samples using Fluorescence Spectroscopy and Parallel Factor Anyalysis, XP-002662372, Analytical Chemistry, Apr. 10, 2005, pp. 2210-2217, vol. 77, No. 7., American Chemical Society.

Anonymous, Laser invention is Used to Fingerprint Oil, XP-002662374, Aramco ExPat News, Feb. 3, 2010, pp. 2-3, http://www.aramcoexpats.com/articles/2010/02/laser-invention-is-used-to-fingerprint-oil/.

* cited by examiner

METHODS OF PREPARING LIQUID BLENDS FOR BUILDING CALIBRATION CURVES FOR THE EFFECT OF CONCENTRATION ON LASER-INDUCED FLUORESCENCE INTENSITY

RELATED APPLICATION

This application is a divisional of, and claims priority to and the benefit of, U.S. patent application Ser. No. 12/815,465, filed on Jun. 15, 2010, titled "Apparatus and Method for Replicating Liquid Blends and Identifying the Ratios of Their Liquid Ingredients," the disclosure of which is incorporated herein by reference in its entirety.

BACKGROUND

1. Field of the Invention:

The invention relates to a small volume apparatus and a trial-and-error method for identifying and replicating original target liquid blends of unknown ratios by employing laser-induced fluorescence spectroscopy.

2. Description of the Related Art:

Laser-induced Fluorescence (LIF) spectroscopy is a sensitive investigative tool for gases, liquids, and solids. As with many other analytical techniques, however, the fluorescence methods often require some sort of reference samples to which the target samples can be compared. The comparisons are usually made either in the intensities of specific lines or bands, in the occurrence of specific lines or bands, or in the shapes of specific absorption or emission spectra. Such comparative fluorescence methods are commonly used in countless applications in the field of material inspections.

Liquids, such as non-contaminated or non-blended hydrocarbon fuels (e.g., jet fuel, gasoline, and diesel fuel), are characterized with fluorescence emission spectra of distinct shapes when excited with ultraviolet light. When such fuels become contaminated or blended with another type of fuel, however, their spectral shapes suffer alterations depending on the fluorescence spectral/temporal characteristics of the contaminants. The contaminants can be in the form of small amounts of other types of fuels which have remained, for example, in multi-purpose pipelines or refined oil storage tanks, or even in the form of small amounts of the same fuel but having different sulfur contents, which commonly happens in diesel fuel distribution operations and storage. The contaminants can also be in the form of weathered fuels mixed with fresh ones or in the form of some chemicals that cannot readily be identified. In most of these cases, the contaminants in the hydrocarbon fuels can be identified by making a comparison in the shapes of the fluorescence emission spectra between the contaminated and the uncontaminated samples. An example of such comparative procedure is ASTM method D 3650-93 (Reapproved 2006), which is a standard test for comparison of waterborne petroleum oils by fluorescence analysis. In that method, the identification of the oil is made by direct visual comparison of the sample's fluorescence emission spectrum with the same spectra of possible source samples, all being excited using ultraviolet radiation at 254 nm. In other words, to perform spectral comparisons, whether visual or numerical, measurements must first be performed on a reference sample, or on a set of reference samples, in order to generate the necessary reference data to which the measurements from the unknown sample will be compared. In many cases, the needed information will not be only the type of the contaminants but also their volume ratios in the blend, i.e., their concentrations. This, in turn, will necessitate the additional steps of preparing sets of standard blends with pre-known concentrations and performing measurements on them to produce the necessary calibration curves.

Other have developed methods and systems for measuring liquids using spectroscopic techniques, such as U.S. Pat. No. 5,480,775 to Ito, et al., which describes an apparatus and method for detecting a specimen in a liquid after dying the specimen with a fluorescence dye; U.S. Pat. No. 6,272,376 to Marcu, et al., which discloses a method for the characterization of organic material using time-resolved laser-induced fluorescence spectroscopy; U.S. Pat. No. 6,700,660 to Sabsabi, et al., which describes a method and apparatus for in-process liquid analysis by laser-induced plasma spectroscopy; and U.S. Pat. No. 5,198,871 to Hill, Jr., et al., which uses fluorescence spectral comparisons to obtain an indication of the physical characteristics of specimen. None of the systems or methods described in such patents are designed to involve a trial-and-error procedure for replicating a blend of unknown ratios or to be a technique for building calibration curves without involving standard blends of pre-known ratios.

In U.S. Pat. No. 6,952,259 (hereinafter "the '259 patent") to Pible, et al., a method of detecting the presence of a serum liquid within the context of bioassays, particularly in immunological tests, is disclosed. The methods described in the '259 patent are implemented in two ways. In the first disclosed method, the mix is prepared and a fluorescence measurement is carried out on it to produce a calculated reference value $R_0$, which is some function of the measured signal. The serum liquid is then pipetted into the mix and a fluorescence measurement is carried out to monitor the corresponding calculated value R. Finally, a comparison is made between R and R0, such that if $R \geq kR0$ then it is an indication that there are no pipetting errors, wherein k is a coefficient relating to statistical fluctuations. However, if $R < kR0$ then this would be an indication that there are errors in the pipetting operation and, consequently, the mix with the serum liquid must be discarded. In this latter case, the process will be repeated again by using a new amount of the previously prepared mix (whose R0 value had already been calculated) and by pipetting a new amount of the serum liquid into the mix.

In the second disclosed method of implementation in the '259 patent, the mix is dispensed into a multitude of separate wells and the procedure leading to the determination of R0 is done for only a small number of those wells, while the procedure leading to the determination of R, after pipetting the serum, is done for each of the wells followed by a check for the R checking the condition of $R \geq kR0$ in each case. The objective of the '259 patent is to ensure that the prepared sample (mix+serum) does not contain the wrong amount of serum every time the preparation is made. The concept of operation is based on a sorting-by-comparison process in which a multitude of identical (mix+serum) fluids are compared, one at a time, to some reference fluid. Those (mix+serum) fluids that meet the criterion are considered acceptable while those that do not are discarded. Thus, the idea of the systems and methods described in the '259 patent is not aimed at adjusting the amount of serum in the mix in the failure cases.

A few patents describe methods and systems for liquid blending. The purpose of such systems, however, is to introduce techniques for dispensing accurate liquid volumes into the blending container. A good representative of such system is described in U.S. Pat. No. 5,125,533 (hereinafter "the '533 patent") to Gayer, et al., which discloses a variable blending dispenser intended for fuel dispensers. In the '533 patent, volumetric data observed by flow meters would be the means by which the blend ratios are controlled.

A need exists for methods and systems that are capable of identifying liquid blends in which the blend ratios of the components are not known beforehand. It would be beneficial if the methods and systems could reproduce the blends once the blend composition has been identified.

SUMMARY

In view of the foregoing, embodiments of the present invention include methods for creating replicas of an original target liquid blend whose blend ratios are not known beforehand, and related apparatuses. The concept of the method is based on repeated measurement of the fluorescence spectrum of a formed blend and frequent comparison between this fluorescence spectrum of the formed blend and the fluorescence spectrum of the original target liquid blend, i.e., the blend to be replicated. The dispensing of liquid ingredients is done on a trial-and-error basis such that the choice of the liquid ingredient to be dispensed is determined based on the visual comparison between the spectra of the original target liquid blend and the formed blends. The process continues until the measured fluorescence spectrum of the formed blend substantially matches, within a pre-defined range of error, the spectrum of the original target liquid blend. The formed blend that has a spectrum that matches, within a pre-defined range of error, the spectrum of the original target liquid blend is the final formed blend. Hence, the final formed blend in the container is generally a replica of the target blend, which can be used in further chemical analysis if needed. By measuring volumes dispensed into the container from the liquid dispensers to create the final formed blend, the blend ratios of the final formed blend can be easily calculated thus defining the blend of the original target liquid blend.

The methods of the present invention are based on mixing known volumes of the liquid ingredients of the blend inside a quartz container while repeatedly monitoring the resulting laser-induced fluorescence (LIF) spectra. The mixing is done on a trial-and-error basis with the objective of ultimately producing a blend whose LIF spectrum substantially matches that of the original unknown blend, which is considered the target blend. By measuring the volumes dispensed into the quartz container, the original blend ratios can be easily determined.

Embodiments of the present invention can be used to quickly and easily determine the blend ratios in an unknown mix without having to prepare calibration curves, and also to produce a replica of unknown blends for use in further analysis. In addition, the invention can be used as a calibration curve builder without having to prepare separate standard solutions.

The methods and apparatuses of the present invention can also be used to obtain measurements for building calibration curves, such as Fluorescence Intensity versus Concentration curves, by dispensing pre-calculated amounts of the ingredient liquids into the container, instead of preparing a full set of mixes having different concentrations.

In accordance with an embodiment of the invention, there is provided a method of identifying and replicating unknown ratios of an original target fuel blend. The method includes a step of placing a liquid handling device in a 90° or a front-surface excitation-emission geometry with respect to a light source and a fluorescence detector unit based on a type of the original target fuel blend in use. The method further includes steps of measuring a first, laser-induced fluorescence spectrum of the original target fuel blend to obtain a target spectrum, and storing and displaying the target spectrum on a background of a personal computer using spectroscopy software. Further, the method includes steps of dispensing pre-calculated amounts of fuel ingredients relative to a total amount of volume present in a vessel to produce consecutive fuel blends of desired ratios in the vessel, and measuring a second laser-induced fluorescence spectrum for each of the consecutive fuel blends to produce blend spectrums. Calibration curves of laser-induced fluorescence intensity versus fuel blend concentration are built based on the blend spectrums and the dispensed pre-calculated amounts of the fuel ingredients for identifying and replicating the unknown ratios of the original target fuel blend.

In accordance with an embodiment, the method further includes steps of replacing the original target fuel blend of unknown ratios with a known volume of one fuel ingredient of the original target fuel blend, and measuring the second laser-induced fluorescence spectrum of the one fuel ingredient. The method further includes a step of comparing a spectral shape and an intensity of the second laser-induced fluorescence spectrum of the one fuel ingredient with those of the original target fuel blend.

In accordance with an embodiment, the method further includes steps of dispensing small amounts of the fuel ingredients from corresponding fuel dispensers to produce a fuel blend, and monitoring the second laser-induced fluorescence spectrum of the fuel blend. The method further includes a step of comparing the second laser-induced fluorescence spectrum to the first laser-induced fluorescence spectrum of the original target fuel blend.

In accordance with an embodiment, the method further includes a step of dispensing a fuel ingredient into the vessel in a consecutive manner until a match is achieved between the second laser-induced fluorescence spectrum of the produced fuel blend and the first laser-induced fluorescence spectrum of the original target fuel blend, using a comparison between the second laser-induced fluorescence spectrum of the produced fuel blend and the first laser-induced fluorescence spectrum of the original target fuel blend, as a guide.

In accordance with an embodiment, the method further includes a step of recording the pre-calculated amounts of the fuel ingredients dispensed into the vessel to calculate the desired ratios of the consecutive fuel blends.

In accordance with an embodiment, the step of monitoring the second laser-induced fluorescence spectrum of the fuel blend includes monitoring techniques selected from the group consisting of time-resolved monitoring, synchronous scan monitoring, total luminescence monitoring, or combinations thereof.

In accordance with an embodiment, the step of measuring the laser-induced fluorescence spectrum of the one fuel ingredient includes measurement techniques selected from the group consisting of a plasma technique, an absorbance technique, a reflectance technique, or combinations thereof In accordance with an embodiment, the step of measuring the laser-induced fluorescence spectrum of the one fuel ingredient includes generating results that are expressed in numerical values, in visual displays of spectra, or combinations thereof In accordance with an embodiment, if more than two components are present in the target blend, the methods described herein are equally applicable. The methods described herein can be used with blends having more than two components.

The feedback data is based on the fluorescence measurement and can originate from a variety of fluorescence monitoring techniques such as time-resolved, synchronous scan, total luminescence, and others. Other optical measurements such as plasma, absorbance, and reflectance techniques can also be used to generate the feedback data depending on the application needed. In addition, the measurements and the comparisons between the measurements can be expressed in the form of either specific numerical values or in the form of mere visual displays of spectra.

BRIEF DESCRIPTION OF DRAWINGS

So that the manner in which the above-recited features, aspects and advantages of the invention, as well as others that will become apparent, are attained and can be understood in detail, more particular description of the invention briefly summarized above can be had by reference to the embodiments thereof that are illustrated in the drawings that form a part of this specification. It is to be noted, however, that the appended drawings illustrate some embodiments of the invention and are, therefore, not to be considered limiting of the invention's scope, for the invention can admit to other equally effective embodiments.

DETAILED DESCRIPTION

Laser-induced fluorescence (LIF) techniques can be used in the detection of liquids that can fluoresce because of their high sensitivity to light. Refined liquid petroleum oils are known to fluoresce when excited by ultraviolet or visible light. The refined petroleum products are characterized by broad LIF spectra whose intensities, spectral ranges, and temporal responses, all depend on the group of hydrocarbon components that have been extracted during the specific thermal distillation processes for each type of product. If the refined oil becomes blended or contaminated with other types of refined oil, its LIF fluorescence spectrum will be altered and, thus, the blending or contamination can be detected by using suitable fluorescence techniques.

In embodiments of the present invention, methods and an apparatus are provided that recreate an unknown refined oil blend by allowing drops of separate blend ingredients to be mixed while at the same time monitoring the LIF of the resulting blend each time the blend is modified by the drops. An objective of the whole operation is to ultimately create a blend whose LIF spectrum substantially matches that of the unknown refined oil blend, which is referred to hereinafter as the target blend. The end result in the container will be a replica of the original target blend sample in addition to information about the blend ratios.

As an embodiment of the present invention, a method for identifying blend ratios in an original target liquid blend using fluorescence is provided. In this embodiment, the original target liquid blend is exposed to ultraviolet laser radiation to excite particles in the original target liquid blend. A first fluorescence of the original target liquid blend is then measured to obtain a target spectrum. A second fluid is then placed in a vessel. A predetermined quantity of a first substance is added to the second fluid to create a blend. A second fluorescence of the blend is measured to produce a blend spectrum, which is then compared to the target spectrum. The method steps of adding a predetermined quantity of the first substance to the second fluid, measuring the second fluorescence, and comparing the blend spectrum to the target spectrum are repeated until the blend spectrum substantially matches the target spectrum. A cumulative quantity of the first substance and a cumulative quantity of the second substance present in the blend having the blend spectrum that substantially matches the target spectrum are then recorded.

In an aspect, the step of adding a predetermined quantity of the first substance to the second fluid to create a blend includes adding a predetermined quantity of a second substance to the second fluid. In another aspect, the step of adding a predetermined quantity of the first substance to the second fluid to create a blend includes adding an additional quantity of the second fluid to the blend.

Various types of measurement techniques can be used to measure the first and second fluorescence. In an aspect, the first fluorescence and the second fluorescence are each measured using laser induced fluorescence spectroscopy. Other measurement techniques that can be used will be apparent to those of skill in the art and are to be considered within the scope of the present invention.

In an aspect, embodiments of the present invention can include estimating the quantity of the first substance, the second substance (if present), and the second fluid required to cause the second fluorescence to be approximately the same as the first fluorescence.

In an aspect, if more than two components are present in the target blend, the methods described herein are equally applicable. The methods described herein can be used with blends having more than two components.

In an aspect, the method embodiments of the present invention can further include the step of calculating blend ratios for the original target liquid blend based upon the cumulative quantity of the first substance and the cumulative quantity of the second substance present in the liquid blend.

In an aspect, the method embodiments of the present invention can further include the step of creating calibration curves based upon the cumulative quantity of the first substance and the cumulative quantity of the second substance present in the liquid blend.

In an aspect, the method embodiments of the present invention can further include the step of replicating blend ratios for the original target liquid blend based upon the cumulative quantity of the first substance and the cumulative quantity of the second substance present in the liquid blend.

In an aspect, the method embodiments of the present invention can further include the step of displaying the target spectrum, the blend spectrum, or a combination thereof on a personal computer display.

As another embodiment of the present invention, a method for identifying blend ratios in an original target liquid blend using fluorescence is provided. In this embodiment, the original target liquid blend is exposed to ultraviolet laser radiation to excite particles in the original target liquid blend. A first fluorescence of the original target liquid blend is measured using laser induced fluorescence spectroscopy to obtain a target spectrum. A second fluid is then placed in a vessel. A predetermined quantity of a first substance is added to the second fluid to create a blend. A second fluorescence of the blend is measured using laser induced fluorescence spectroscopy to produce a blend spectrum. The blend spectrum is compared to the target spectrum. The method steps of adding a predetermined quantity of the first substance to the second fluid, measuring the second fluorescence, and comparing the blend spectrum to the target spectrum are repeated until the blend spectrum substantially matches the target spectrum. A quantity of the first substance, the second substance, and the second fluid required to cause the second fluorescence to approximately match the first fluorescence is then estimated. A cumulative quantity of the first substance and a cumulative quantity of the second substance present in the blend having the blend spectrum that substantially matches the target spectrum is then recorded.

As yet another embodiment of the present invention, a method of identifying and replicating unknown ratios of original target liquid blends is provided. In this embodiment, a liquid handling device is placed in a 90° or a front-surface excitation-emission geometry with respect to a light source and a fluorescence detector unit depending on the type of blend in use. A laser-induced fluorescence spectrum of a target unknown blend sample is obtained. The spectrum are stored and displayed on a background of a personal computer using suitable spectroscopy software.

In embodiments of the present invention, the methods described herein can include the step of replacing a blend of unknown ratios with a known volume of one liquid ingredient of the blend, measuring its laser-induced fluorescence, and comparing its spectral shape and intensity with those of the target unknown blend.

In embodiments of the present invention, the methods described herein can include the step of dispensing small amounts of liquid ingredients from their corresponding liquid dispensers and essentially simultaneously monitoring a resulting laser-induced fluorescence spectrum from a formed blend, and continuously comparing it to the spectrum of the target unknown blend.

In embodiments of the present invention, the methods described herein can include the step of dispensing a liquid ingredient into a container in a consecutive manner until a substantial match, within a pre-defined range of error, is achieved between the spectrum of the created blend and the spectrum of the target unknown blend using a comparison between the spectrum of the created blend and the spectrum of the target unknown blend as a guide.

The pre-defined range of error can vary, depending on the process conditions and the specifications used in particular processes. In embodiments of the present invention, the pre-defined range of error between the spectra of the target liquid blend and the formed blend is less than 10%; alternatively, less than 5%; alternatively, less than 2%; or alternatively, less than 1%.

In embodiments of the present invention, the methods described herein can include the step of recording the amounts of volumes dispensed into the container from each liquid dispenser in order to calculate blend ratios.

In embodiments of the present invention, the methods described herein can include the step of dispensing pre-calculated amounts of liquid ingredients relative to a total amount of volume already present in the vessel to produce consecutive blends of desired ratios in the same vessel for the purpose of building calibration curves of laser-induced fluorescence intensity versus blend concentration.

Various monitoring techniques can be used to essentially simultaneously monitor the resulting laser-induced fluorescence spectrum from the formed blend. In an aspect, the monitoring can be performed using monitoring techniques comprising time-resolved monitoring, synchronous scan monitoring, total luminescence monitoring, or combinations thereof. Other suitable monitoring techniques will be apparent to those of skill in the art and are to be considered within the scope of the present invention.

Various measuring techniques can be used to measure the laser-induced fluorescence from the formed blend. In an aspect, the measuring can be performed using measurement techniques comprising plasma technique, absorbance technique, reflectance technique, or combinations thereof. Other suitable measuring techniques will be apparent to those of skill in the art and are to be considered within the scope of the present invention.

In an aspect, the measuring results can be expressed in numerical values, in visual displays of spectra, or combinations thereof. Other suitable means to express the measuring results will be apparent to those of skill in the art and are to be considered within the scope of the present invention.

In an aspect, the methods and systems described herein can also be used to prepare liquid blends of any desired ratios in a cumulative manner, which is useful in certain applications such as in building calibration curves for the effect of concentration on the LIF fluorescence intensity.

Figure 1:
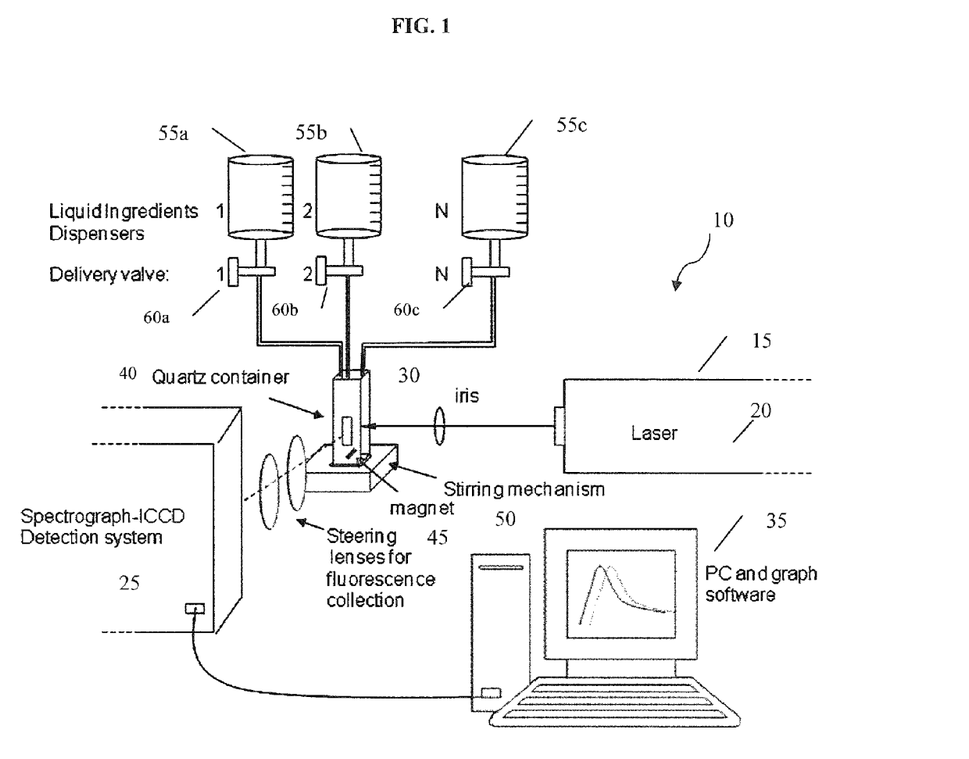
FIG. 1 is a schematic diagram of an apparatus, in accordance with an embodiment of the invention.

Besides the method embodiments described herein, apparatus embodiments are also provided as embodiments of the present invention. For example, as an embodiment of the present invention and as shown in FIG. 1, an apparatus 10 for identifying blend ratios in an original target liquid blend using fluorescence is provided.

In embodiments of the present invention, the apparatus 10 includes a light source 15, a light dispersing device 20, a fluorescence emission detector 25, a liquid handling device 30, and a display 35. The light source 15 is used for generating a pulse of ultraviolet laser radiation. The light source 15 is suitable for exciting the types of liquids being mixed. The light-dispersing device 20 is used for exposing the original target liquid blend to the pulse of ultraviolet laser radiation to excite particles in the original target liquid blend. The fluorescence emission detector 25 is used for measuring a first fluorescence of the original target liquid blend to obtain a target spectrum and measuring a second fluorescence of the blend to produce a blend spectrum. The fluorescence emission detector 25 is a detection system for dispersing, detecting, and measuring the fluorescence emitting from the excited liquid mixture. The liquid handling device 30 is used in which a second fluid and a predetermined quantity of a first substance to the second fluid can be placed to create a blend. The liquid handling device 30 includes a mini liquid handler by which the liquids are mixed in known volumes. The display 35 is operative to display fluorescence spectra.

In an aspect, embodiments of the present invention can also include a computer software for the computational analysis of the recorded spectra. Suitable computer software that can be used in embodiments of the present invention will be apparent to those of skill in the art and are to be considered within the scope of the present invention.

In an aspect, the apparatus 10 also includes a liquid container 40 that is transparent to visible and ultraviolet light; a magnet bar 45 and magnetic stirrer 50; a plurality of liquid dispensers 55a, 55b, 55c corresponding to liquid ingredients to be blended; a volume controlled dispensing valve 60a, 60b, 60c for each liquid dispenser 55a, 55b, 55c; and a valve controller for controlling the volume controlled dispensing valve for each liquid dispenser (not shown). The liquid container 40 is transparent to the type of light to be used in the LIF measurements. The number of liquid dispensers 55 and volume-controlled delivery valves 60 can vary and corresponds to the number of liquid ingredients to be used in the trial-and-error mixing.

EXAMPLE 1

A kerosene and diesel fuel blend was used to demonstrate the effectiveness of the methods and systems of the present invention. Refined liquid petroleum oils, such as kerosene and diesel, were used because they are known to fluoresce when excited by ultraviolet or visible light. A standard quartz cuvette of dimensions 10 mm×10 mm×40 mm was used as the liquid container 40, and two syringe infusion pumps were used as the liquid dispensers 55a, 55b and delivery valves 60a, 60b. The syringe infusion pumps can be either single separate syringe pumps or one multiple syringe pump. The pumps used in the present demonstration were two single syringe pumps of model KDS 100 from KD Scientific, each having a Hamilton-brand glass syringe of 10-ml volume and a narrow Luer-lock stainless steel needle capable of dispensing accurate volumes of as low as 0.01 ml. Once the kerosene and diesel fuel liquids were dispensed through the needles they were sent to the quartz cuvette 40 through flexible tubing. The stirring mechanism used in the present demonstration was a small regular magnet bar 45 placed inside the cuvette 40 and a magnetic stirrer 50 located right underneath the body of the cuvette 40. The kerosene and diesel fuel liquids were dispensed by using simple menu-driven buttons on the KDS100 instruments, which basically allowed for choosing the volume of the liquid and the rate at which it was be dispensed, which was chosen to be the fastest possible rate.

The source of excitation light used in the embodiments of the present invention can be arbitrary and can depend on the type of liquids in the blend whose excited fluorescence is to be measured. The wavelength of the light source, its intensity, its coherence characteristics, its type as in pulsed or continuous, and also its pulse temporal width in the case of pulsed light sources are all factors that should be considered when selecting the source of the excitation light. In the present example, the source of light was chosen to be an ultraviolet pulsed laser with a wavelength of 266 nm, which was emitted from the forth harmonic of a Nd:YAG laser. The laser-pulse temporal width was about 8 ns and its energy was kept fixed at 25 mJ per pulse. Other types of light sources having different properties will be apparent to those of skill in the art and are to be considered within the scope of the present invention.

The geometry of the excitation-emission setup is also a parameter that can be changed in the invention depending on the type of liquids used. For liquids of small extinction coefficients; i.e., liquids through which the excitation light does not become totally absorbed within small depths at the surface, 90° excitation-emission geometry can be utilized. In such case the fluorescence emission will be measured at 90° relative to the direction of the excitation light. For relatively opaque liquids; i.e., liquids that absorb all the excitation light very near to the surface as in the case of crude petroleum oils, front surface geometry should be used. In this case the excitation light must be directed at the same surface of the cuvette from which the fluorescence emission is measured. In the present example, the laser light could penetrate to depths larger than 0.5 cm inside the kerosene/diesel fuel blend, and hence the 90° geometry was utilized as shown in FIG. 1.

The type of fluorescence detection system that can be used in embodiments of the present invention can vary depending on the expected spectrum characteristics of the original target liquid blend. For example, a scanning mono-chromator coupled with a photomultiplier tube is one possibility. This combination can be used with or without a signal processor/analyzer depending on whether time-gating is needed or not. Another possible system, which was the one used in the present example kerosene/diesel fuel, is a spectrograph coupled with a time-gated Intensified Charge Coupled Device (ICCD). The LIF spectrum of the kerosene/diesel fuel blend was expected to be a broad spectrum with no sharp features superimposed on it and thus a low resolution spectrograph was adequate to use in this particular case; i.e., a spectrograph equipped with a low resolution diffraction grating (150 grooves/mm).

As known in the art it is customary to match the dispersed spectrum coming out from the diffraction grating with the pixels on the ICCD readout module such that each pixel gives information about the intensity at a particular wavelength. When displayed on a Personal Computer (PC) using appropriate spectroscopy software the output resulting from the detection system will display two-dimensional Fluorescence Intensity versus Wavelength graphs. This type of spectra was used in the present example for the live-monitoring process.

In this example, the unknown original target liquid blend was first placed inside the cuvette and its LIF spectrum was excited by the light source, measured by the detection system, and displayed as a background spectrum onto the PC monitor. This spectrum was the target spectrum to be replicated using the trial-and-error process described herein. The unknown original target liquid blend was then removed from the cuvette and one of the liquid ingredients from the liquid dispensers replaced it inside the cuvette. The trial-and-error process was started by measuring the LIF spectrum of that liquid ingredient and comparing it to the target spectrum. If they were different either in intensity or in shape, a certain volume from the other liquid ingredient dispenser was dispensed inside the cuvette and the LIF spectrum of the blend was measured after a sufficient time was given for stifling the blend. The new LIF spectrum was then compared with the target spectrum and depending on the results a certain volume from one of the liquid ingredients was be dispensed inside the cuvette again, and so on. The blend ratio in the cuvette was thus always varying and so was the measured LIF spectrum. The objective was to produce a blend whose LIF spectrum matched that of the target.

Figure 2:
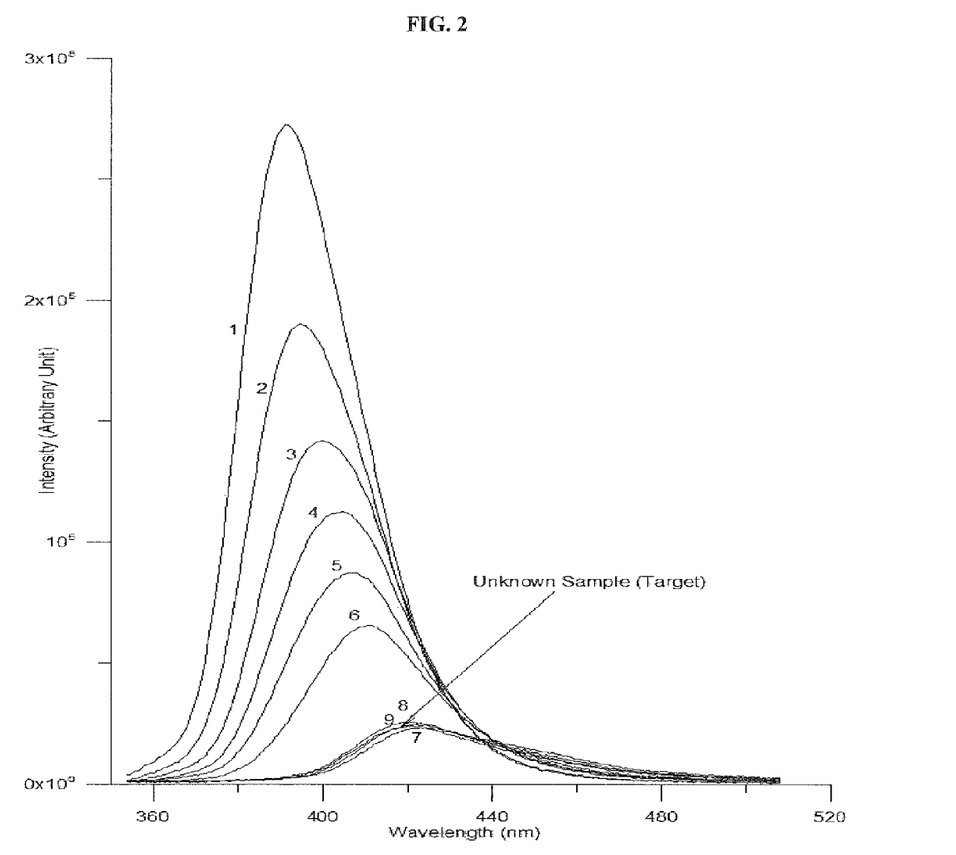
FIG. 2 is a graphic illustration of a laser-induced fluorescence spectra for a kerosene-Diesel fuel blend, while it is being blended, in accordance with an embodiment of the invention. The numbers on the spectra designate the sequence in which the volume-dispensing trials were carried out. The spectrum of the original unknown target blend was replicated after 9 trials.

Referring to FIG. 2 it is shown a set of LIF spectra showing a demonstration of how the live-monitoring of the LIF spectra was used in the invention. In this example, a liquid Target sample was prepared by contaminating pure kerosene with a small amount of diesel fuel and was then placed inside the cuvette. The LIF spectrum of that liquid target sample was recorded and was kept in the background of the PC monitor through appropriate spectroscopy software. The liquid target sample in the cuvette was then replaced with pure kerosene of known volume (2 ml) whose LIF spectrum was, in turn, measured under the same exact conditions of geometry and spectroscopic parameters. The resulting LIF spectrum of pure kerosene from this first trial was designated with numeral 1 in FIG. 2. Successive volumetric amounts from the diesel fuel dispenser were then dispensed into the cuvette as described in Table I, and the LIF spectra resulting from these trial blends were measured. These spectra were labeled with numerals from 2 to 7 on FIG. 2. At the end of the seventh trial the total volume of the blend has become 2.27 ml of which 2.00 ml was kerosene and 0.27 ml was diesel fuel; in other words, the diesel fuel contamination in the blend had reached 11.89%. This ratio, however, caused the LIF spectrum of the blend to overshoot the spectrum of the Target sample. To get back closer to the target, pure kerosene was dispensed into the cuvette. A volume of 1.00 ml of kerosene dispensed into the cuvette changed the percentage of the diesel fuel to 8.26%, but still the LIF spectrum of this eighth trial was not an exact match for that of the target blend. Finally, in the ninth trial a volume of 0.05 ml of diesel fuel was dispensed into the cuvette and the resulting LIF spectrum ended up matching that of the target blend as can be seen in FIG. 2. Hence, it was concluded that the original target sample blend consists of about 90.36% kerosene and 9.64% diesel fuel. In addition, the blend in the cuvette became an exact replica of the original target blend and can be used in any further analysis.

TABLE I

Details of the blend mixing of Kerosene and Diesel fuel demonstration experiment

| Trials | Amount of Kerosene dispensed into cuvette (ml) | Amount of Diesel fuel dispensed into cuvette (ml) | Total volume of the blend accumulated inside the cuvette (ml) | Percentage of Kerosene in the blend (%) | Percentage of Diesel fuel in the blend (%) |
|---|---|---|---|---|---|
| 1 | 2.00 | — | 2.00 | 100 | 0 |
| 2 | — | 0.01 | 2.01 | 99.50 | 0.50 |
| 3 | — | 0.01 | 2.02 | 99.01 | 0.99 |
| 4 | — | 0.01 | 2.03 | 98.52 | 1.48 |
| 5 | — | 0.01 | 2.04 | 98.04 | 1.96 |
| 6 | — | 0.03 | 2.07 | 96.62 | 3.38 |
| 7 | — | 0.20 | 2.27 | 88.11 | 11.89 |
| 8 | 1.00 | — | 3.27 | 91.74 | 8.26 |
| 9 | — | 0.05 | 3.32 | 90.36 | 9.64 |

EXAMPLE 2

As indicated previously, the methods and systems described herein can be used to prepare liquid blends of any desired ratios in a cumulative manner. In other words, the methods and systems described herein can be used to prepare serial blends (or solutions) of standard pre-known ratios one at a time using only one container. This can be done by calculating the necessary dispensing volumes of the liquid ingredients relative to the total volume already available in the quartz container.

To demonstrate this aspect of the present invention, Table II provides data illustrating the calculations used to prepare liquid blends. In this example, it was desired to produce blends of kerosene/diesel fuels in the following consecutive concentrations: kerosene/diesel in v/v=100/0, 99/1, 98/2, 97/3, 96/4, and 95/5, so that the LIF spectra could be measured for each concentration in a consecutive manner for the purpose of building a calibration curve of fluorescence intensity versus blend concentration. Starting from 2 ml pure kerosene in the cuvette, the LIF spectrum was acquired as per the procedure described above, then to get 1% diesel fuel in the blend an amount of 0.0205 ml of diesel fuel was dispensed, which made the total volume 2.0205 ml. Now to produce 2% diesel fuel in the blend, another amount of 0.0207 of diesel fuel was dispensed and so on.

TABLE II

Example of dispensing pre-calculated volumes of Kerosene and Diesel fuel in order to produce a systematic increase in the percentage of Diesel fuel in the blend as desired.

| Trials | Desired Kerosene/ Diesel Fuel (v/v %) | Amount of Kerosene to be dispensed (ml) | Amount of Diesel fuel to be dispensed (ml) | Total volume of blend accumulated inside the cuvette (ml) |
|---|---|---|---|---|
| 1 | 100/0 | 2.0000 | — | 2.0000 |
| 2 | 99/1 | — | 0.0205 | 2.0205 |
| 3 | 98/2 | — | 0.0207 | 2.0412 |
| 4 | 97/3 | — | 0.0205 | 2.0617 |
| 5 | 96/4 | — | 0.0242 | 2.0859 |
| 6 | 95/5 | — | 0.0239 | 2.1098 |

The method of identifying a contaminated liquid is by reconstructing it from its pure ingredients, which can be done by dropping carefully measured minute amounts of the liquid and the suspected contaminating liquid(s) in a trial-and-error manner while simultaneously monitoring the fluorescence spectrum of the blend in each step. The amounts of dropped liquids are important parameters because they eventually calculate the percentages.

In an aspect, the contaminated liquid and the liquid contaminant are blended together and there is no external solvent used. The result of the fluorescence intensity, and also the fluorescence spectral shape, depends on both of the blended liquids. The calibration curve in this case is a xy-plot constructed by relating the intensity of the overall fluorescence in specific spectral ranges as a function of the relative concentration of the two liquids. Because both of the liquids affect the spectral shape in a collective manner there will be a choice of calibration curves that can be employed and not only a single one.

In an aspect, the calibration curves generated are typically not linear since both liquids contribute to the signal.

In an aspect, at least two syringes are used to introduce controlled amounts of liquids into the quartz cuvette onto which the laser (or the light source) is impinging. In other words, the cuvette is the measurement station itself. It is a part of the on-line measuring instrument. The syringes are not used one time only, they are also part of the on-line measurement as they are operated continuously on a trial-and-error basis.

In an aspect, the resulting fluorescence spectrum is observed. The intensity of the whole spectra is divided by the intensity of a particular wavelength in one of the fluorescence spectra of one blend.

Figure 3:
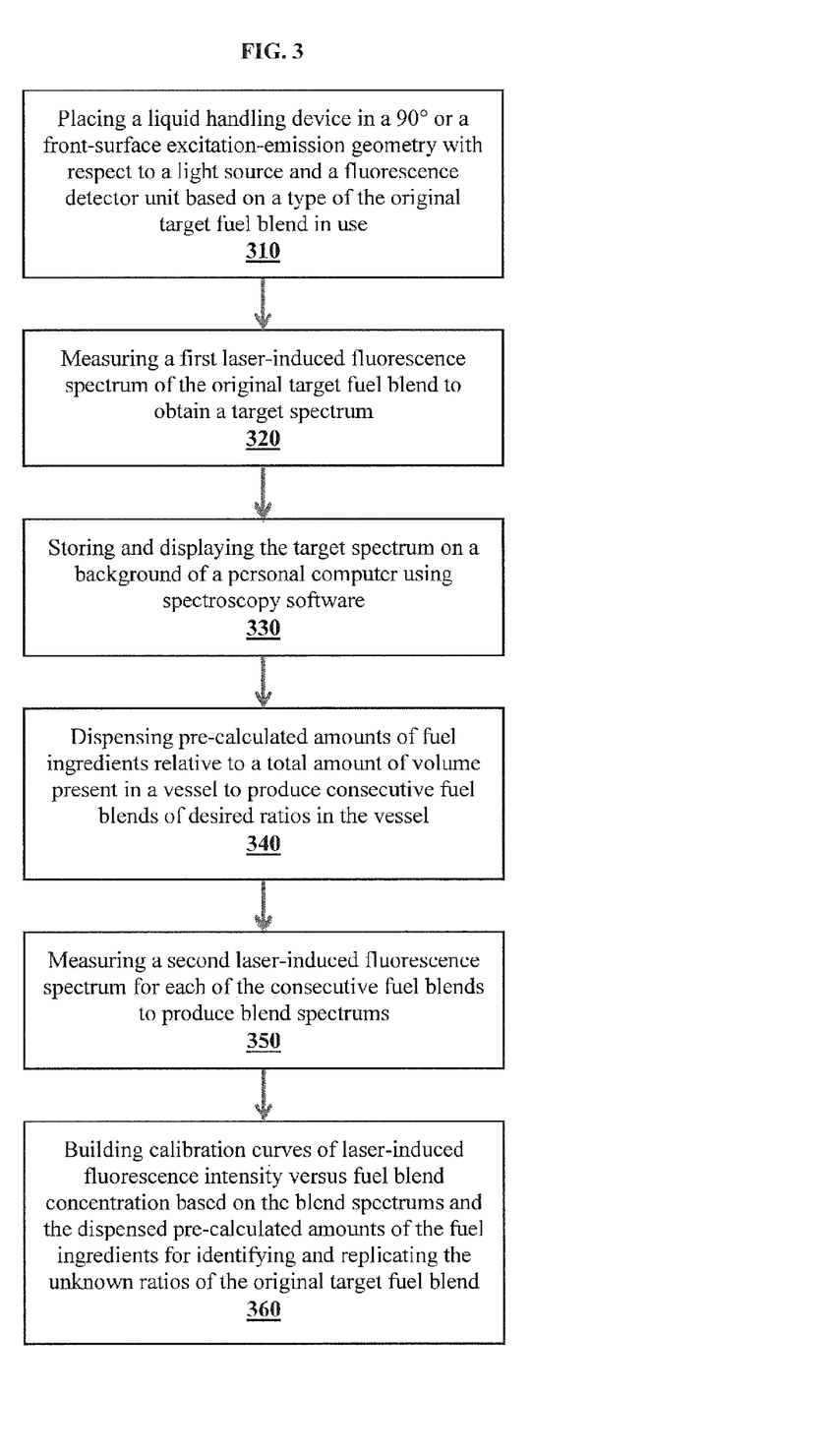
FIG. 3 is a flow diagram of a method of identifying and replicating unknown ratios of an original target fuel blend, in accordance with an embodiment of the invention.

Referring to FIG. 3, in accordance with an embodiment of the invention, there is provided a method of identifying and replicating unknown ratios of an original target fuel blend. The method includes a step of placing, at 310, a liquid handling device in a 90° or a front-surface excitation-emission geometry with respect to a light source and a fluorescence detector unit based on a type of the original target fuel blend in use. The method further includes steps of measuring, at 320, a first laser-induced fluorescence spectrum of the original target fuel blend to obtain a target spectrum, and storing and displaying, at step 330, the target spectrum on a background of a personal computer using spectroscopy software. Further, the method includes steps of dispensing, at step 340, pre-calculated amounts of fuel ingredients relative to a total amount of volume present in a vessel to produce consecutive fuel blends of desired ratios in the vessel, and measuring, at step 350, a second laser-induced fluorescence spectrum for each of the consecutive fuel blends to produce blend spectrums. Calibration curves of laser-induced fluorescence intensity versus fuel blend concentration are built, at step 360, based on the blend spectrums and the dispensed pre-calculated amounts of the fuel ingredients for identifying and replicating the unknown ratios of the original target fuel blend.

In accordance with an embodiment, the method further includes steps of replacing the original target fuel blend of unknown ratios with a known volume of one fuel ingredient of the original target fuel blend, and measuring the second laser-induced fluorescence spectrum of the one fuel ingredient. The method further includes a step of comparing a spectral shape and an intensity of the second laser-induced fluorescence spectrum of the one fuel ingredient with those of the original target fuel blend.

In accordance with an embodiment, the method further includes steps of dispensing small amounts of the fuel ingredients from corresponding fuel dispensers to produce a fuel blend, and monitoring the second laser-induced fluorescence spectrum of the fuel blend. The method further includes a step of comparing the second laser-induced fluorescence spectrum to the first laser-induced fluorescence spectrum of the original target fuel blend.

In accordance with an embodiment, the method further includes a step of dispensing a fuel ingredient into the vessel in a consecutive manner until a match is achieved between the second laser-induced fluorescence spectrum of the produced fuel blend and the first laser-induced fluorescence spectrum of the original target fuel blend, using a comparison between the second laser-induced fluorescence spectrum of the produced fuel blend and the first laser-induced fluorescence spectrum of the original target fuel blend, as a guide.

In accordance with an embodiment, the method further includes a step of recording the pre-calculated amounts of the fuel ingredients dispensed into the vessel to calculate the desired ratios of the consecutive fuel blends.

In accordance with an embodiment, the step of monitoring the second laser-induced fluorescence spectrum of the fuel blend includes monitoring techniques selected from the group consisting of time-resolved monitoring, synchronous scan monitoring, total luminescence monitoring, or combinations thereof In accordance with an embodiment, the step of measuring the laser-induced fluorescence spectrum of the one fuel ingredient includes measurement techniques selected from the group consisting of a plasma technique, an absorbance technique, a reflectance technique, or combinations thereof.

In accordance with an embodiment, the step of measuring the laser-induced fluorescence spectrum of the one fuel ingredient includes generating results that are expressed in numerical values, in visual displays of spectra, or combinations thereof While the invention has been shown in only a few of its forms, it should be apparent to those skilled in the art that it is not so limited but susceptible to various changes without departing from the scope of the invention. Accordingly, it is intended to embrace all such alternatives, modifications, and variations as fall within the spirit and broad scope of the appended claims.

Those skilled in the art will recognize that many changes and modifications can be made to the method of practicing the invention without departing the scope and spirit of the invention. In the drawings and specification, there have been disclosed embodiments of the invention and, although specific terms are employed, they are used in a generic and descriptive sense only and not for the purpose of limitation, the scope of the invention being set forth in the following claims. The invention has been described in considerable detail with specific reference to these illustrated embodiments. It will be apparent, however, that various modifications and changes can be made within the spirit and scope of the invention as described in the foregoing specification. Furthermore, language referring to order, such as first and second, should be understood in an exemplary sense and not in a limiting sense. For example, it may be recognized by those skilled in the art that certain steps can be combined into a single step.

What is claimed is:

1. A method of identifying and replicating unknown ratios of an original target fuel blend, the method comprising steps of:
   placing a liquid handling device in a 90° or a front-surface excitation-emission geometry with respect to a light source and a fluorescence detector unit based on a type of the original target fuel blend in use;
   measuring a first laser-induced fluorescence spectrum of the original target fuel blend to obtain a target spectrum;
   storing and displaying the target spectrum on a background of a personal computer using spectroscopy software;
   dispensing pre-calculated amounts of fuel ingredients relative to a total amount of volume present in a vessel to produce consecutive fuel blends of desired ratios in the vessel;
   measuring a second laser-induced fluorescence spectrum for each of the consecutive fuel blends to produce blend spectrums; and
   building calibration curves of laser-induced fluorescence intensity versus fuel blend concentration based on the blend spectrums and the dispensed pre-calculated amounts of the fuel ingredients for identifying and replicating the unknown ratios of the original target fuel blend.

2. A method of claim 1, further comprising steps of:
   replacing the original target fuel blend of unknown ratios with a known volume of one fuel ingredient of the original target fuel blend;
   measuring the second laser-induced fluorescence spectrum of the one fuel ingredient; and
   comparing a spectral shape and an intensity of the second laser-induced fluorescence spectrum of the one fuel ingredient with those of the original target fuel blend.

3. A method of claim 2, wherein the step of measuring the laser-induced fluorescence spectrum of the one fuel ingredient includes measurement techniques selected from the group consisting of a plasma technique, an absorbance technique, a reflectance technique, or combinations thereof.

4. A method of claim 2, wherein the step of measuring the laser-induced fluorescence spectrum of the one fuel ingredient includes generating results that are expressed in numerical values, in visual displays of spectra, or combinations thereof.

5. A method of claim 1, further comprising steps of:
   dispensing small amounts of the fuel ingredients from corresponding fuel dispensers to produce a fuel blend;
   monitoring the second laser-induced fluorescence spectrum of the fuel blend; and
   comparing the second laser-induced fluorescence spectrum to the first laser-induced fluorescence spectrum of the original target fuel blend.

6. A method of claim 5, wherein the step of monitoring the second laser-induced fluorescence spectrum of the fuel blend includes monitoring techniques selected from the group consisting of time-resolved monitoring, synchronous scan monitoring, total luminescence monitoring, or combinations thereof.

7. A method of claim 1, further comprising a step of:
   dispensing a fuel ingredient into the vessel in a consecutive manner until a match is achieved between the second laser-induced fluorescence spectrum of the produced fuel blend and the first laser-induced fluorescence spectrum of the original target fuel blend, using a comparison between the second laser-induced fluorescence spectrum of the produced fuel blend and the first laser-induced fluorescence spectrum of the original target fuel blend, as a guide.

8. A method of claim 1, further comprising a step of:
recording the pre-calculated amounts of the fuel ingredients dispensed into the vessel to calculate the desired ratios of the consecutive fuel blends.

* * * * *